US00PP18216P2

(12) United States Plant Patent
van Kleinwee

(10) Patent No.: US PP18,216 P2
(45) Date of Patent: Nov. 13, 2007

(54) *LOBELIA* PLANT NAMED 'LOBTRAWI'

(50) Latin Name: *Lobelia erinus*
Varietal Denomination: Lobtrawi

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/435,077

(22) Filed: May 16, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,708 P2 * 6/2002 Westhoff ..... Plt./263

OTHER PUBLICATIONS

UPOV ROM GTITM Computer Database GTI Jouve Retrieval Software 2006/04 Citations for Lobtrawi.*

* cited by examiner

*Primary Examiner*—Wendy C. Haas
(74) *Attorney, Agent, or Firm*—Bruce Vrana

(57) ABSTRACT

A new and distinct cultivar of *Lobelia* plant named 'Lobtrawi' characterized by its spreading plant habit, strong branching, large flower size and white flower color.

1 Drawing Sheet

Latin name of the genus and species of the plant claimed: *Lobelia erinus.*
Varietal denomination: 'Lobtrawi'.

BACKGROUND OF THE NEW PLANT

The present invention comprises a new and distinct *Lobelia* plant botanically known as *Lobelia erinus* and referred to by the cultivar name 'Lobtrawi'.

The new cultivar is propagated by cuttings resulting from the cross between 'A925' and 'A950.' 'A925' is a white flower color selection of our own breeding, having a spreading habit, strong growth, good branching plant habit and being early flowering. 'A950' is a white flower color selection of our own breeding, having a strong growth, semitrailing plant habit and not very branching. Neither 'A925' or 'A950' has been patented.

As a result of this cross the present cultivar was created from a single plant in 2001 in Enkhuizen, Netherlands and has been repeatedly asexually reproduced by cuttings in Enkhuizen, Netherlands over a five year period. It has been found to retain its distinctive characteristics through successive propagations and this novelty appears to be firmly fixed.

DESCRIPTION OF THE DRAWING

This new *Lobelia* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Lobelia.* The data which defines these characteristics were collected from asexual reproductions carried out in Enkhuizen, Netherlands. The plant history was taken on 20 week old plants.

Color readings were taken in the laboratory under ambient light. Color references are primarily to The R.H.S. Color Chart of The Royal Horticultural Society of London.

TABLE 1

DIFFERENCES BETWEEN 'LOBTRAWI' AND THE MOST RESEMBLING VARIETY

| | 'Lobtrawi' | 'Weslowei' (U.S. Pat. No. 12,708) |
|---|---|---|
| Plant | | |
| height | 25 cm | 20 cm |
| width | 45 cm | 45 cm |
| shape | Spreading | Spreading to upright |
| Flower color | | |
| upper surface | N155A occasionally 95D | N155A occasionally 97B |
| lower surface | N155A | N155A |
| flower tube | N155A | N155A |
| Petiole | Not present | Present |

The plant:

*Classification*—Botanical: *Lobelia erinus.*

*Female parent.*—A seedling named 'A925' is one of our seedlings from our A-generation of plants bred in 1999.

*Male parent.*—A seedling named 'A950' is one of our seedlings from our A-generation of plants bred in 1999.

*Growth habit.*—Upright.

*Plant height.*—25 cm.

*Spreading area of plant.*—45 cm.

*Growth rate.*—Strong growth.

*Strength.*—Good.

*Branching character.*—Freely branching and lateral branching at every node. Pinching will enhance branching. Branches strong and flexible.

*Blooming period.*—From May until October.

The stem:

*Diameter.*—1.5 mm.

*Texture.*—Smooth, slightly pubescent, glossy.

*Color.*—RHS 143A.

*Length of internode.*—10–25 mm, depending on light conditions where the plant is grown, and the age of the stem.

*Shape.*—Triangular.

The foliage:

*Shape.*—Leaves simple, generally symmetrical and flat. Broadly ovate with rounded apex, obtuse and attenuate base and crenate margin in young plant; more lanceolate with entire margin in mature plant.

*Texture.*—Slightly pubescent, glossy.

*Width.*—In young plant 12 mm, mature plant 5 mm.

*Color.*—Upper surface: RHS 137B, RHS 137C in young leaves. Lower surface: RHS 137C, RHS 137 in young leaves.

*Petiole.*—Not present.

The flower:

*Type and habit.*—Flowers form at apical axils, usually one flower per axil. Flowers labiate, upper lip consisting of two small petals and lower lip consisting of three larger and broader petals.

*Lastingness.*—10–14 days depending on temperature. Petals are fused at base into a tube. Freely and continuously flowering, around 100–150 flowers. Flowers face outward. Texture, slightly pubescent. Oblong shape with acute apex and entire margin.

*Flower.*—Width: Upper petals 1 mm, lower petals 6 mm. Length: Upper petals 6 mm, lower petals 8 mm. Depth: 13 mm.

*Texture.*—Smooth pubescent.

*Buds.*—Length: 10 mm. Diameter: 3 mm. Form: Tubular. Color: Light green.

*Flower color.*—Upper surface: N155A occasionally 95D. Lower surface: RHS N155A. Flower tube: RHS N155A.

*Sepals.*—No. of sepals: 5. Length: 6 mm. Width: 0.5 mm. Texture: Smooth, slightly pubescent. Color: RHS 143C.

*Flower stem.*—Length: 15–18 mm. Angle: 45 degrees. Stength: Rigid, flexible. Color: RHS 143A.

*Flower throat.*—Color: Upper N155A. Lower N155A at base of the lower petals, where the throat starts, there are 2 yellow marking into the throat (length 8 mm, width 0.5 mm, RHS 2A). Texture: Whiskered. Depth: 7 mm.

Reproductive organs:

*Androecium.*—Stamen number: 5. Anther shape: Oblong. Anther length: 2 mm. Anther color: RHS 9B. Amount of pollen: Moderate. Pollen color: RHS 9B.

*Gynoecium.*—Pistil length: About 8 mm. Stigma shape: Bilobate. Stigma diameter: 1 mm. Stigma color: N80C. Style color: RHS 150B. Ovary color: RHS 143C.

Seed development: Some seed development has been observed on plants of the new *Lobelia*.

Seed:

*Color.*—Brown.

*Shape.*—Round.

*Size.*—Very small, like dust.

*Amount per seed pod.*—Approximately 2000.

Fruit:

*Fruit size.*—Diameter: 2 mm. Length: 5 mm.

*Fruit color.*—RHS 146B.

Disease resistance: No susceptibility or resistance to fungal, bacterial, or viral pathogens has been noted.

What is claimed is:

1. A new and distinct cultivar of *Lobelia* plant named 'Lobtrawi', as substantially illustrated and described herein.

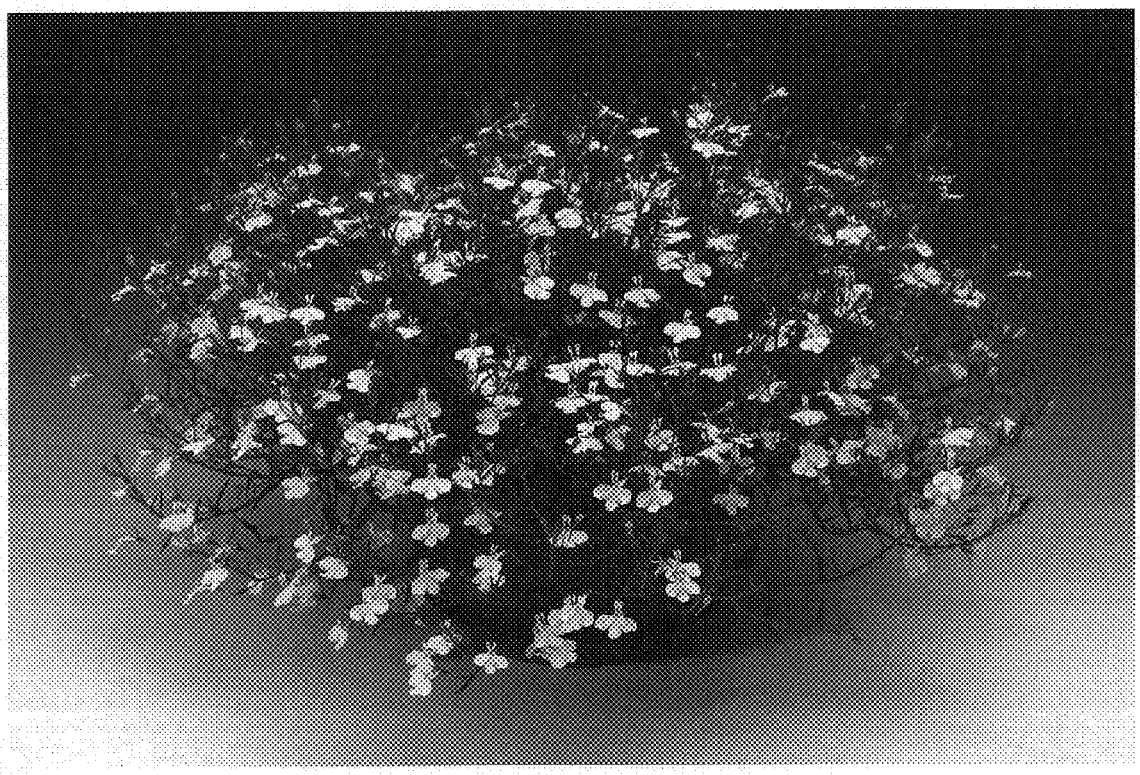

* * * * *